(12) United States Patent
Kato et al.

(10) Patent No.: US 6,939,510 B2
(45) Date of Patent: Sep. 6, 2005

(54) ANTI-PROTISTA PREPARATION

(75) Inventors: Hiroyuki Kato, Tokyo (JP); Tadayoshi Yazaki, Yamanashi (JP); Tokihiko Maruyama, Yamanashi (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 667 days.

(21) Appl. No.: 09/839,357

(22) Filed: Apr. 23, 2001

(65) Prior Publication Data

US 2001/0048916 A1 Dec. 6, 2001

(30) Foreign Application Priority Data

Apr. 25, 2000 (JP) .......................................... 2000-123433
Mar. 30, 2001 (JP) .......................................... 2001-099320

(51) Int. Cl.[7] ............................ A61L 2/00; A01N 59/08
(52) U.S. Cl. ...................... 422/28; 210/755; 210/954; 210/764; 422/1; 422/39; 422/40; 424/661
(58) Field of Search .............................. 422/1, 28, 39, 422/40; 210/755, 954, 764; 424/661

(56) References Cited

U.S. PATENT DOCUMENTS 4,043,911 A * 8/1977 Melnick et al. ............. 210/755
4,400,374 A 8/1983 Cardarelli .................... 424/78
4,983,389 A 1/1991 Levy ........................... 424/404
5,006,267 A 4/1991 Vaughn et al. ............... 210/755

FOREIGN PATENT DOCUMENTS

| EP | 149 302 A | 7/1981 |
| EP | 0 733 304 A2 | 9/1996 |
| EP | 0 845 480 A1 | 6/1998 |
| JP | 6-1701 | 1/1994 |
| JP | 11-246309 | 9/1999 |

* cited by examiner

*Primary Examiner*—Krisanne Jastrzab
(74) *Attorney, Agent, or Firm*—Armstrong, Kratz, Quintos, Hanson & Brooks, LLP.

(57) ABSTRACT

The present invention provides a sustained-releasing anti-protista preparation, including using a water-insoluble or difficulty water soluble and water-wettable polymer compound which is solid at room temperature as a sustained-releasing substrate material, a method for a preparation of the sustained-releasing anti-protista preparation, including kneading a water-insoluble or difficulty water soluble and water-wettable polymer compound which is solid at room temperature with an anti-protista substrate, and a sustained-releasing anti-protista preparation for a waterway, including using a water insoluble or difficulty water soluble and water-wettable polymer compound which is solid at room temperature as a sustained-releasing substrate material.

9 Claims, 1 Drawing Sheet

ANTI-PROTISTA PREPARATION

BACKGROUND OF INVENTION

The present invention relates to a preparation (composition) which can inhibit propagation of a protista, for instance, in a waterway such as a drain in a refrigerator, a freezer etc. by releasing gradually anti-protista substance contained therein.

The main reason for giving bad influence by a protista such as bacteria, fungi and algae upon living environments is generally existence of water, and water in this sense has included waste water of human life and waste water from factories whose BOD value is high (which are classified into the first group), and rain water, condensation water of vapor formed by change of temperature, circulating water by heat exchangers, circulating water by fixed temperature circulating type bath tubs, condensation water generated from heat exchangers and condensation water generated from air compressors (which are classified into the second group), and so on.

Among them, in those which are classified into the first group, nutrients for bacteria, fungi and algae are originally contained, and in those which are classified into the second group, any means against bacteria, fungi and algae (e.g. using chlorine effective to city water) is originally not adopted.

And, in the first group water, bacteria, fungi and algae propagate themselves, and also in the second group water, they propagate themselves when certain conditions (such as temperature, free contact with outdoor atmosphere and continuous supply of nutrients) are fulfilled, so that there is caused such a problem as generation of bad smell, coloring, pollution and narrowing or blocking drain channels.

For the purpose of solving such problem as above, there have generally been adopted such technologies as a physical removal means comprising scraping off mechanically accumulated protista and/or its metabolites and a chemical treatment comprising adding or spraying periodically antibacterial agents, antifungi agents, antialgae agents, etc. However, those technologies usually require large amount of time and manpower, and further in the chemical treatment, use of very strong inorganic acids, inorganic alkaline substances, oxidizing agents, reducing agents, etc. are generally necessary and therefore environmental pollution and damage to health of workers by the chemicals themselves have generally been feared. Additionally, a long-lasting effect cannot be expected by those technologies and thus these treatments are necessarily required frequently.

SUMMARY OF INVENTION

The present invention has been accomplished under the circumstances as mentioned above and its object is to provide a novel sustained-releasing anti-protista preparation (composition) which can prevent and remove more simply bad influences by propagation of protista such as bacteria, fungi and algae in waterways such as drain of a refrigerator, freezer, etc. for a long period of time.

The present invention has been completed for the purpose of solving the above problem, and relates to "(1) A sustained-releasing composition of anti-protista substance comprising: a water-wettable polymer compound having solubility of 1 g or less per 1 liter of water; and an anti-protista substance selected from the group of consisting of a heavy metal and a compound containing the metal, a cationic surface active quaternary type ammonium salt containing a long chain alkyl group, an amphoteric surface active agent containing a long chain alkyl group, a quinoline derivative, an organic nitrogen-sulfur compound, a benzene derivative, a biguanidine compound, sorbic acid and its salt, ε-polylysine, hinokitiol, various kinds of formalin donor, and chloroisocyanuric acid and its salt, further, an amount of the anti-protista substance in the composition is 10 to 90 (wt % of the total composition), (2) A sustained-releasing composition of anti-protista substance, which is obtained by kneading a water-wettable polymer compound having solubility of 1 g or less per 1 liter of water with an anti-protista substance which is selected from the group of consisting of a heavy metal and a compound containing the metal, a cationic surface active quaternary type ammonium salt containing a long chain alkyl group, an amphoteric surface active agent containing a long chain alkyl group, a quinoline derivative, an organic nitrogen-sulfur compound, a benzene derivative, a biguanidine compound, sorbic acid and its salt, ε-polylysine, hinokitiol, various kinds of formalin donor, and chloroisocyanuric acid and its salt, (3) A method for killing of or inhibiting of propagation of a protista in a waterway, comprising allowing flowing water in a waterway to contact with the sustained-releasing antibacterial of the composition as (1)."

Namely, the present inventors have extensively studied for looking for a method capable of inhibiting propagation of bacteria, fungi and algae by a simple manner for a long period of time to arrive at the finding that when an anti-protista substance included in a wettable polymer compound having specific properties is placed in a waterway such as drain of a refrigerator, freezer, etc. the said anti-protista substance is gradually released into water to attain the above purpose, and the present invention has been completed on the basis of this finding.

BRIEF DESCRIPTION OF THE DRAWING

In FIG. 1, --- ◊ --- shows the dissolution curve in the preparation 1, -☆- shows that in the preparation 2, -Δ- shows that in the preparation 3, --X-- shows that in the preparation 4, --○-- shows that in the preparation 5, -X- shows that in the preparation 6, -+- shows that in the preparation 7, -*- shows that in the preparation 8, -□- shows that in the preparation 9, -♦- shows that in the preparation 10, --□-- shows that in the preparation 11 and -○- shows that in the preparation 12, respectively.

PREFERRED EMBODIMENTS OF INVENTION

Figure 1:
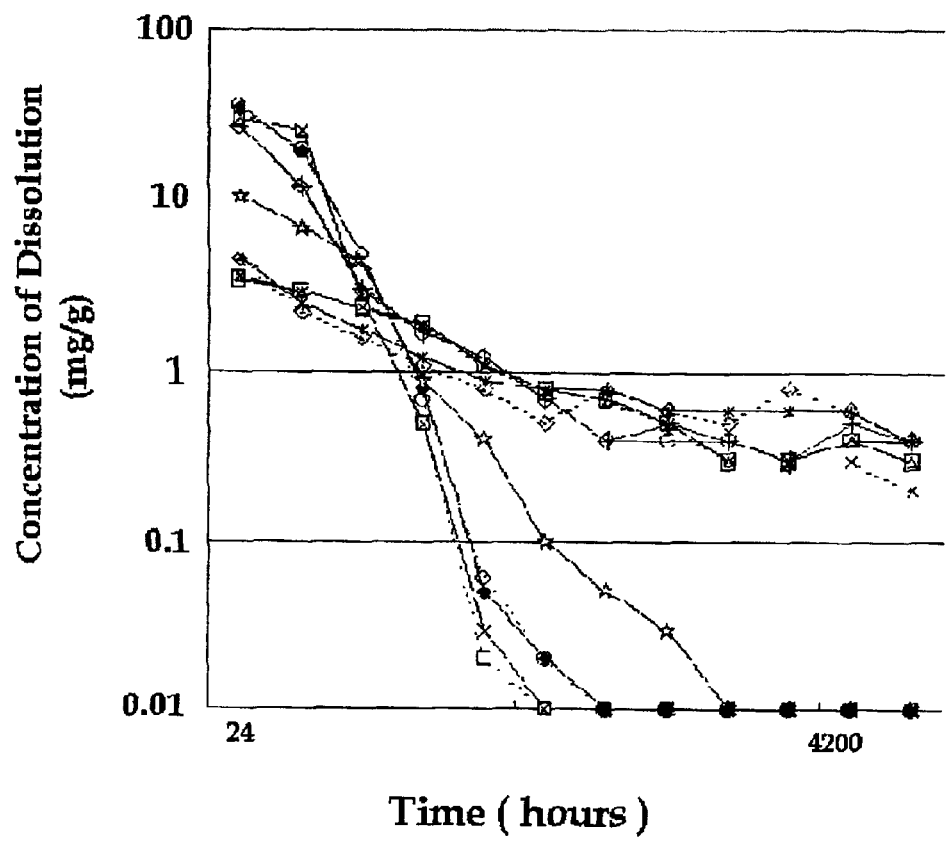
FIG. 1 is for showing dissolution concentrations at each time of the preparations obtained in Experimental Example 1.

The anti-protista substance of the present invention may be any one which can prevent and inhibit propagation of a protista such as bacteria, fungi and algae, and includes a heavy metal such as zinc, copper and silver and compounds containing the metal; a cationic surface active quaternary type ammonium salt containing a long chain alkyl group of 10 to 24 carbon atoms such as a dodecyl group, a cetyl group and a stearyl group, including an aliphatic quaternary ammonium salt, pyridinium salts, imidazolium salts, a benzalconium salt and a benzetonium salt (for instance, salt with a halogen ion such as chlorine ion, bromine ion and iodine ion, a phosphoric acid type ion such as phosphoric acid ion, phosphonic acid ion and a mono- or dialkyl phosphoric acid ester ion); an amphoteric surface active agent containing a long chain alkyl group of 10 to 24 carbon atoms such as an alkyl di(aminoethyl)glycine and its salt (for instance, salt with an alkaline metal such as sodium and potassium, ammonium and hydrochloric acid) and an imidazolinium betain; a quinoline derivative such as 8-quinolinol and its copper complex and decalinium salt (for instance, salt with a halogenohydrogenic acid such as hydrochloric acid); an organic nitrogen-sulfur compound such as methylenebisthiocyanate, dimethyldithiocarbamate, thiabendazole, isothiazolinone compounds and pyrithione salts (for instance, salt with an alkaline metal such as sodium and potassium, zinc and copper); a benzene derivative such as p-oxybenzoic acid esters, benzoic acid and its salt (for instance, salt with an alkaline metal such as sodium and potassium and ammonium), trichlorocarbanilide, trichlorohydroxydiphenyl ether, o-phenylphenol and its salt (for instance, salt with an alkaline metal such as sodium and potassium), chlorophenol compounds, salicylic acid and its salt (for instance, salt with an alkaline metal such as sodium and potassium and ammonium) and methylisopropylphenols; a biguanidine compound such as a chlorohexidine salts (for instance, salt with hydrochloric acid and gluconic acid) and a polyhexamethylenebiguanide salt (for instance, salt with hydrochloric acid and gluconic acid); sorbic acid and its salt (for instance, salt with an alkaline metal such as sodium and potassium and ammonium); ε-polylysine; hinokitiol; various kinds of formalin donors; chloroisocyanuric acid and its salt (for instance, salt with an alkaline metal such as sodium and potassium), etc., among which a cationic surface active quaternary type ammonium salt containing a long chain alkyl group of 10 to 24 carbon atoms such as a dodecyl group, a cetyl group and a stearyl group, including an aliphatic quaternary ammonium salt, pyridinium salts, imidazolium salts, a benzalconium salt and a benzetonium salt (concrete salts are the same as above); an amphoteric surface active agent containing a long chain alkyl group of 10 to 24 carbon atoms such as an alkyl di(aminoethyl) glycine and its salt (concrete salts are the same as above) and an imidazolinium betain; a benzene derivative such as p-oxybenzoic acid esters, benzoic acid and its salt (concrete salts are the same as above), trichlorocarbanilide, trichlorohydroxydiphenyl ether, o-phenylphenol and its salt (concrete salts are the same as above), chlorophenol compounds, salicylic acid and its salt (concrete salts are the same as above) and methylisopropylphenols; sorbic acid and its salt (concrete salts are the same as above); chloroisocyanuric acid and its salt (concrete salts are the same as above), etc. are preferable, and a cationic surface active quaternary type ammonium salt containing a long chain alkyl group of 10 to 24 carbon atoms such as a dodecyl group, a cetyl group and a stearyl group, including an aliphatic quaternary ammonium salt, pyridinium salts, imidazolium salts, a benzalconium salt and a benzetonium salt (concrete salts are the same as above) are more preferable and cetyl pyridinium chloride is further more preferable. Those substances may be used alone or in a suitable combination of two or more thereof.

An amount of the anti-protista substance to be used is generally 10 to 90 (wt % of the total composition), preferably 20 to 70 (wt % of the total composition), more preferably 30 to 70 (wt % of the total composition) in terms of the content in the sustained-releasing anti-protista preparation (composition).

As a substrate material for the sustained-releasing preparation (composition) of the present invention, use is made of a wettable and water-insoluble or hardly soluble polymer compound which is solid at room temperature. The "difficulty water soluble" means that "solubility in 1 liter of water is 1 g or less, preferably 0.1 g or less", and the "wettable" means "capable of being wetted with water to cause wetting under immersion upon contacting with water". Because of those properties, the anti-protista substance included in the polymer compound can gradually release upon contacting with water. Examples of those polymer compounds are a polyacrylic acid salt such as sodium polyacrylate, potassium polyacrylate and calcium polyacrylate; a cross-linked polyacrylic acid salt such as Carbopol™ (manufactured and sold by BF Good Rich) and HIVISWAKO™ (manufactured and sold by Wako Pure Chemical Industries, Ltd.); a starch type polymer such as a starch/acrylonitrile copolymer and a starch/methyl methacrylate copolymer; a cellulose type polymer such as a celulose/acrylonitrile copolymer and a cellulose/sodium monochloroacetate copolymer; a polyvinylalcohol type polymer such as polyvinylalcohol and a polyvinylalcohol/polyacrylic acid copolymer; a cellulose derivative such as a hydroxymethyl cellulose salt, a hydroxyethyl cellulose salt, a hydroxypropyl cellulose salt, a carboxymethyl cellulose salt and a carboxypropyl cellulose salt; a polyacrylic acid ester modified by silicone such as a polydimethylsiloxane/polymethyl acrylate; a polymethacrylic acid ester modified by silicone such as polydimethylsiloxane/polymethyl methacrylate; polysaccharides such as curdlan; a hydroxy carboxylic acid type polymer such as polylactic acid, polyglycolic acid and a lactic acid/glycolic acid copolymer; a polyacrylamide type polymer; polyoxyethylene polymer; polyvinyl acetate; a cyclodextrin and its derivatives; cellulose fiber; rayon fiber, etc., among which a polyacrylic acid salt such as sodium polyacrylate, potassium polyacrylate and calcium polyacrylate; a cross-linked polyacrylic acid salt such as Carbopol™ (manufactured and sold by BF Good Rich) and HIVISWAKO™ (manufactured and sold by Wako Pure Chemical Industries, Ltd.); a starch type polymer such as a starch/acrylonitrile copolymer and a starch/methyl methacrylate copolymer; a cellulose type polymer such as a celulose/acrylonitrile copolymer and a cellulose/sodium monochloroacetate copolymer; a polyvinylalcohol type polymer such as polyvinylalcohol and a polyvinylalcohol/ polyacrylic acid copolymer; a cellulose derivative such as a hydroxymethyl cellulose salt, a hydroxyethyl cellulose salt, a hydroxypropyl cellulose salt, a carboxymethyl cellulose salt and a carboxypropyl cellulose salt; a polyacrylic acid ester modified by silicone such as a polydimethylsiloxane/ polymethyl acrylate; a polymethacrylic acid ester modified by silicone such as polydimethylsiloxane/polymethyl methacrylate; a polyacrylamide type polymer; polyvinyl acetate are preferable, a polyvinylalcohol type polymer such as polyvinylalcohol and a polyvinylalcohol/polyacrylic acid copolymer are more preferable, and polyvinylalcohol is further more preferable. Those polymers may be used alone or in a suitable combination of two or more thereof.

A molecular weight of the substrate for the sustained-releasing prepration is not specifically limited so long as it can attain the object of the present invention, and is generally 4,000 to 1000,000. An amount of the polymer compound to be used is generally 90 to 10 (wt % of the total composition), preferably 80 to 30 (wt % of the total composition), more preferably 70 to 30 (wt % of the total composition) in terms of the content in the sustained-releasing anti-protista preparation (composition).

A silicone content in the acrylic acid ester modified by silicone as the substrate for the sustained-releasing preparation (composition) of the present invention is generally 10 to 30 %, preferably 15 to 25 %, and its molecular weight is generally 100,000 to 200,000, preferably 100,000 to 150, 000.

A kind of salt in the cellulose derivative as the substrate for the sustained-releasing preparation (composition) of the present invention includes a salt with an alkaline metals such as sodium and potassium; a salt with an alkaline earth metal such as magnesium and calcium; a salt with aluminum; a salt with zinc, etc., among which a salt with sodium and potassium are preferable. Its molecular weight is generally 50,000 to 150,000, preferably 50,000 to 100,000.

Polyvinyl alcohol as the substrate of the sustained-releasing preparation (composition) of the present invention may be completely saponified one or partially saponified one, and the saponification degree of the latter is generally 80 to 95, preferably 80 to 90, and its polymerization degree is generally 100 to 4,000, preferably 800 to 3,000, more preferably 2000 to 3000.

The cross-linked polyacrylic acid salt as the substrate of the sustained-releasing preparation (composition) of the present invention includes one having three dimensional structure formed by cross-linking an acrylic acid salt by a cross-linking agent, which is obtained by polymerization of an acrylic acid salt in which a carboxyl group is neutralized with sodium hydroxide, etc. in the presence of other monomer (a cross-linking agent) containing a polymerizable double bond, one which is obtained by polymerizing acrylic acid in the presence of a cross-linking agent to give a polymer having three dimensional structure formed by the cross-linking agent and then neutralizing a part of or all of the carboxylic acid in the polymer with sodium hydroxide, etc. to give the corresponding salt, etc. The cross-linking agent includes methylenebisacrylamide, trimethylpropane triacrylate, ethyleneglycol diacrylate, polyethyleneglycol diacrylate (n=4), etc., among which methylenebisacrylamide and ethyleneglycol diacrylate are preferable. A molecular weight of those cross-linked polyacrylic acid salts is generally 100,000 to 1000,000, preferably 200,000 to 700,000.

A form of the sustained-releasing preparation (composition) of the present invention is not specifically limited, so long as the preparation (composition) can stably be placed in a waterway, etc., and the preparation is generally molded into pellet, block, tablet, granule, etc.

The anti-protista preparation (composition) of the present invention is prepared, for instance, as follows.

Namely, first of all, the anti-protista substance and the substrate for sustained-releasing are kneaded with each other in water, acetone or other polar solvent. In this stage, there may be added, as the need arises, an agent for heightening anti-bacterial effect such as sodium ethylenediamine tetraacetate, an agent for heightening compatibility such as an alcohol including methanol, ethanol, etc, an coloring agent including methylene blue, methyl orange, a natural carotenoid such as coloring agent of Gardenia, Safflower and Annato, and a tal color such as Blue No.1, Green No.3, Red No.2 and Yellow No.4. By adding these coloring agent, they are dissolved with the anti-protista substance in the flowing water, and so the time of exchanging the anti-protista preparation (composition) is found only by checking the presence of their color. Then, the resulting mixture is melted under heating by an autoclave, water bath or other heating device. Heating temperature at the time is generally 30 to 150° C., preferably 50 to 100° C., and the time required for melting depends upon heating temperature and is generally 10 to 100 minutes, preferably 10 to 50 minutes. After melting under heating, the melted solution is dried with or without blowing under normal or reduced pressure, whereby the object preparation (composition) is obtained. The preparation (composition) having the desired size and shape can be obtained by charging the melted solution into a cup or other container having a suitable size in the drying step, and the preparation (composition) in the form of pellet can be obtained by drying the melted solution in the form of plate, followed by cutting at vertical and horizontal directions. Drying temperature is generally 30 to 100° C., preferably 30 to 70° C., and reduced pressure at drying is generally 0 to 30 kPA, preferably 0 to 3 kPA. In the step of melting under heating, it is preferable to heat the resulting mixture until it becomes homogeneous, because the anti-protista substance is homogeneously carried in the anti-protista preparation (composition) of the present invention.

In case of using cellulose fiber, rayon fiber, polyester fiber or other fiber as the substrate for the sustained-releasing preparation (composition), the fiber is immersed in a solution of the anti-protista substance or the substance is wrapped with or included in the fiber, whereby the substance is allowed to exist in the fiber, and then the resultant is dried with or without blowing under normal or reduced pressure, whereby the object preparation (composition) is obtained.

The anti-protista preparation (composition) of the present invention is placed by a suitable manner in a waterway to contact it with flowing water, whereby generation of a protista such as bacteria, fungi and algae in the waterway can be inhibited. The waterway is not specifically limited so long as it is such one wherein a protista such as bacteria, fungi and algae are generated or likely generated, and the effect of the present invention can particularly be recognized in waterways wherein heat and nutrient sources can constantly be supplied and in narrow waterways. The specific places to which the present invention can be applied include ways for waste water (drain) in refrigerators, freezers, ice manufacturing machines and showcases for freezing and cold storage, ways for waste water from air conductors, drainpipes from sinks and bathrooms, ways for waste water from factories, traps of ways for waste water, a flush toilets etc. In those places, a protista such as bacteria, fungi and algae are particularly easily generated because of the above reason, and further when the waterways are narrowed or blocked by accumulation of bacteria, fungi and algae, it is difficult to remove the accumulation, and thus in this sense, the anti-protista preparation of the present invention can show its effect remarkably in such waterways as above.

The preparation (composition) produced by adding an anti-protista substance to the substrate for the sustained-releasing according to the method of the present invention can attain such an effect that bad influences by a protista such as bacteria, fungi and algae can much easily be prevented and removed after a simpler manner for a longer period of time, for example 2 months and over at least, preferably 6 months and over preferably, so that cleaning work of narrow waterways can be omitted and clean environment can be kept to maintain functions of machines and devices.

In the following, the present invention is further explained in details with referring to Examples, Experimental examples and Control examples, but the invention is not limited thereto by any means.

EXAMPLE

Example 1

To a stainless vat of about 2 L volume were added 460 g of ion-exchanged water, 100 g of cetyl pyridinium chloride (manufactured and sold by Wako Pure Chemical Industries, Ltd.), 200 g of polyvinyl alcohol (manufactured and sold by KURARAY CO., LTD. Trade Name: KURARAY Poval PVA-124) and 1 g of disodium ethylenediamine tetraacetate, followed by kneading and melting under heating in an autoclave at 115° C. for 30 minutes. The resulting colorless transparent melted solution was charged in a polypropylene cup of φ50 mm and height 30 mm, and dried under reduced pressure of 2 to 3 kPa at 50° C. for 8 hours to give white cylindrical preparation. This preparation was referred to as Preparation 1.

Example 2

To a stainless vat of about 5 L volume were added 803.5 g of ion-exchanged water, 45 g of cetyl pyridinium chloride (manufactured and sold by Wako Pure Chemical Industries, Ltd.), 150 g of polyvinyl alcohol (manufactured and sold by KURARAY CO., LTD. Trade Name: KURARAY Poval HR-1000) and 1.5 g of disodium ethylenediamine tetraacetate, followed by kneading and melting under heating in an autoclave at 115° C. for 30 minutes. The resulting pale yellow transparent melted solution was dried under reduced pressure of 2 to 3 kPa at 50° C. for 8 hours. The resultant was molded into a plate of about 3 mm thick and further was cut to give white pellet preparation of 10×10×3 mm. This preparation was referred to as Preparation 2.

Example 3

To a beaker of about 2 L volume were added 300 g of ion-exchanged water, 300 g of denatured alcohol, 100 g of cetyl pyridinium chloride (manufactured and sold by Wako Pure Chemical Industries, Ltd.), 300 g of polyvinyl alcohol (manufactured and sold by KURARAY CO., LTD. Trade Name: KURARAY Poval PVA-124) and 1.0 g of disodium ethylenediamine tetraacetate, followed by stirring and melting under heating in a water bath at 70° C. for 10 minutes. The resulting milky white melted solution was charged in a polypropylene cup of φ50 mm and height 30 mm, and dried under reduced pressure of 2 to 3 kPa at 40° C. for 8 hours to give white cylindrical preparation. This preparation was referred to as Preparation 3.

Example 4

To a beaker of about 2 L volume were added 1000 g of acetone and 100 g of polydimethylsiloxane-methyl methacrylate block polymer (manufactured and sold by Wako Pure Chemical Industries, Ltd. Trade Name: PNS-001), followed by stirring to solve at room temperature. Then 100 g of cetyl pyridinium chloride (manufactured and sold by Wako Pure Chemical Industries, Ltd.) was added thereto, followed by dispersing therein by stirring at room temperature. The resulting white dispersion was charged in a polypropylene cup of φ50 mm and height 30 mm, and dried by blowing under normal pressure at 30° C. for 8 hours to give white cylindrical preparation. This preparation was referred to as Preparation 4.

Example 5

To a stainless vat of about 2 L volume were added 360 g of ion-exchanged water, 200 g of benzalconium chloride (manufactured and sold by Kao Corporation, Trade Name: Sanisol C), 200 g of polyvinyl alcohol (manufactured and sold by KURARAY CO., LTD. Trade Name: KURARAY Poval PVA-124) and 1 g of disodium ethylenediamine tetraacetate, followed by kneading and melting under heating in an autoclave at 115° C. for 30 minutes. The resulting colorless transparent melted solution was charged in a polypropylene cup of φ50 mm and height 30 mm, and dried under reduced pressure of 2 to 3 kPa at 50° C. for 8 hours to give white cylindrical preparation. This preparation was referred to as Preparation 5.

Example 6

To a stainless vat of about 2 L volume were added 460 g of ion-exchanged water, 100 g of benzetonium chloride (manufactured and sold by Lonza Ltd., Trade Name: Hyamine), 200 g of polyvinyl alcohol (manufactured and sold by KURARAY CO., LTD. Trade Name: KURARAY Poval PVA-124) and 1 g of disodium ethylenediamine tetraacetate, followed by kneading and melting under heating in an autoclave at 115° C. for 30 minutes. The resulting pale yellow transparent melted solution was charged in a polypropylene cup of φ50 mm and height 30 mm, and dried under reduced pressure of 2 to 3 kPa at 50° C. for 8 hours to give milky whity pale yellow cylindrical preparation. This preparation was referred to as Preparation 6.

Example 7

To a stainless vat of about 2 L volume were added 460 g of ion-exchanged water, 100 g of trichlorohydroxydiphenyl ether (manufactured and sold by Ciba-Geigy Ltd, Trade Name: Irgasan DP300), 200 g of polyvinyl alcohol (manufactured and sold by KURARAY CO., LTD. Trade Name: KURARAY Poval PVA-124) and 1 g of disodium ethylenediamine tetraacetate, followed by kneading and melting under heating in an autoclave at 115° C. for 30 minutes. The resulting yellow transparent melted solution was charged in a polypropylene cup of φ50 mm and height 30 mm, and dried under reduced pressure of 2 to 3 kPa at 50° C. for 8 hours to give milky whity yellow cylindrical preparation. This preparation was referred to as Preparation 7.

Example 8

To a stainless vat of about 2 L volume were added 460 g of ion-exchanged water, 100 g of cetyl pyridinium chloride (manufactured and sold by Wako Pure Chemical Industries, Ltd.) and 200 g of polyvinyl alcohol (manufactured and sold by KURARAY CO., LTD. Trade Name: KURARAY Poval PVA-124), followed by kneading and melting under heating in an autoclave at 115° C. for 30 minutes. The resulting colorless transparent melted solution was charged in a polypropylene cup of φ50 mm and height 30 mm, and dried under reduced pressure of 2 to 3 kPa at 50° C. for 8 hours to give white cylindrical preparation. This preparation was referred to as Preparation 8.

Example 9

To a beaker of about 2 L volume were added 300 g of ion-exchanged water, 300 g of denaturated alcohol, 100 g of cetyl pyridinium chloride (manufactured and sold by Wako Pure Chemical Industries, Ltd.) and 300 g of polyvinyl alcohol (manufactured and sold by KURARAY CO., LTD. Trade Name: KURARAY Poval PVA-124), followed by stirring and melting under heating in a water bath at 70° C. for 10 minutes. The resulting milky white melted solution was charged in a polypropylene cup of φ50 mm and height 30 mm, and dried under reduced pressure of 2 to 3 kPa at 40° C. for 8 hours to give white cylindrical preparation. This preparation was referred to as Preparation 9.

Example 10

To a stainless vat of about 2 L volume were added 360 g of ion-exchanged water, 200 g of benzalconium chloride (manufactured and sold by Kao Corporation, Trade Name: Sanisol C) and 200 g of polyvinyl alcohol (manufactured and sold by KURARAY CO., LTD. Trade Name: KURARAY Poval PVA-124), followed by kneading and melting under heating in an autoclave at 115° C. for 30 minutes. The resulting colorless transparent melted solution was charged in a polypropylene cup of φ50 mm and height 30 mm, and dried under reduced pressure of 2 to 3 kPa at 50° C. for 8 hours to give white cylindrical preparation. This preparation was referred to as Preparation 10.

Example 11

To a stainless vat of about 2 L volume were added 460 g of ion-exchanged water, 100 g of benzetonium chloride (manufactured and sold by Lonza Limited, Trade Name: Hyamine) and 200 g of polyvinyl alcohol (manufactured and sold by KURARAY CO., LTD. Trade Name: KURARAY Poval PVA-124), followed by kneading and melting under heating in an autoclave at 115° C. for 30 minutes. The resulting pale yellow transparent melted solution was charged in a polypropylene cup of φ50 mm and height 30 mm, and dried under reduced pressure of 2 to 3 kPa at 50° C. for 8 hours to give milky whity pale yellow cylindrical preparation. This preparation was referred to as Preparation 11.

Example 12

To a stainless vat of about 2 L volume were added 460 g of ion-exchanged water, 100 g of trichlorohydroxydiphenyl ether (manufactured and sold by Ciba-Geigy Ltd., Trade Name: Irgasan DP300) and 200 g of polyvinyl alcohol (manufactured and sold by KURARAY CO., LTD. Trade Name: KURARAY Poval PVA-124), followed by kneading and melting under heating in an autoclave at 115° C. for 30 minutes. The resulting yellow transparent melted solution was charged in a polypropylene cup of φ50 mm and height 30 mm, and dried under reduced pressure of 2 to 3 kPa at 50° C. for 8 hours to give milky whity yellow cylindrical preparation. This preparation was referred to as Preparation 12.

Experimental Example 1
Sustained-releasing Test

In order to confirm the efficiency of the sustained-releasing preparations, each 40 g of Preparations 1 to 12 obtained in the above Examples was placed on a waterway, ion-exchanged water was flown in the waterway at 1 L/hour, and the ion-exchanged water which was contacted with the preparations was sampled at the predetermined interval. On the samples, concentrations of the anti-protista substance were measured by a high performance liquid chromatography.

The result is shown in FIG. 1. In FIG. 1, --- ◇ --- shows the dissolution curve in the preparation 1, -☆- shows that in the preparation 2, -Δ- shows that in the preparation 3, --X-- shows that in the preparation 4, --○-- shows that in the preparation 5, -X- shows that in the preparation 6, -+- shows that in the preparation 7, -*- shows that in the preparation 8, -□- shows that in the preparation 9, -◆- shows that in the preparation 10, --□-- shows that in the preparation 11 and -○- shows that in the preparation 12, respectively.

From the FIG. 1, the following can be understood; in all of the preparations, the Anti-protista substance is released in the flowing water in an amount of 0.5 mg/g or more after 1272 hours use (about 2 months use) and, particularly, in Preparations 1, 3, 4, 7, 8, 9 and 12, releasing amount is 0.3 mg/g even after 4200 hours use (about 6 months use), and therefore, in all of the preparations, anti-protista effect can be expected, and particularly, in the preparations 1, 3, 4, 7, 8, 9 and 12, the anti-protista effect for 6 months or longer can be expected. In conclusion, all of the preparations have excellent efficiency as anti-protista preparation.

Experimental Example 2
Antibacterial Test

To 4.27 g of GP liquid culture medium (manufactured and sold by Nihon Seiyaku KK.) were added each 15 ml of the releasing solutions on Preparations 1 to 7 after 1 to 6 months, which were obtained in Experimental Example 1, followed by sterilizing at 121° C. for 30 minutes, and 3 kinds of microorganisms (*Aspergillus terrues*; IFO 6346, *Cladosporium cladosporioides*; IFO 6348 and Geotrichum candidum; IFO 5364) were inoculated therein, followed by culturing at 28° C. for 7 days and measuring growing areas of the 3 microorganisms. Growing areas in blanks, culture media obtained by using ion-exchanged water instead of the releasing solutions after the same manner as above on which the 3 microorganisms were incubated, were also measured and compared with those in the above, and inhibition rates by the releasing solutions were calculated. The result is shown in Table 1. In the Table 1, complete inhibition is shown as 100 % and the same growing area as one in the blank is shown as 0%.

TABLE 1

| | microorganism | After 1 month (%) | After 2 month (%) | After 3 month (%) | After 4 month (%) | After 5 month (%) | After 6 month (%) |
|---|---|---|---|---|---|---|---|
| Preparation 1 | IFO 6346 | 100 | 90 | 90 | 80 | 80 | 70 |
| | IFO 6348 | 100 | 100 | 90 | 90 | 90 | 90 |
| | IFO 5364 | 100 | 100 | 100 | 100 | 100 | 100 |
| Preparation 2 | IFO 6346 | 100 | 90 | 90 | 80 | 80 | 70 |
| | IFO 6348 | 100 | 100 | 90 | 90 | 90 | 90 |
| | IFO 5364 | 100 | 100 | 100 | 100 | 100 | 100 |
| Preparation 3 | IFO 6346 | 100 | 90 | 90 | 80 | 80 | 70 |
| | IFO 6348 | 100 | 100 | 90 | 90 | 90 | 90 |
| | IFO 5364 | 100 | 100 | 100 | 100 | 100 | 100 |
| Preparation 4 | IFO 6346 | 100 | 90 | 90 | 80 | 80 | 70 |
| | IFO 6348 | 100 | 100 | 90 | 90 | 90 | 90 |
| | IFO 5364 | 100 | 100 | 100 | 100 | 100 | 100 |
| Preparation 5 | IFO 6346 | 100 | 90 | 90 | 80 | 80 | 70 |
| | IFO 6348 | 100 | 100 | 90 | 90 | 90 | 90 |
| | IFO 5364 | 100 | 100 | 100 | 100 | 100 | 100 |
| Preparation 6 | IFO 6346 | 100 | 90 | 90 | 80 | 80 | 70 |

TABLE 1-continued

|  | microorganism | After 1 month (%) | After 2 month (%) | After 3 month (%) | After 4 month (%) | After 5 month (%) | After 6 month (%) |
|---|---|---|---|---|---|---|---|
|  | IFO 6348 | 100 | 100 | 90 | 90 | 90 | 90 |
|  | IFO 5364 | 100 | 100 | 100 | 100 | 100 | 100 |
| Preparation 7 | IFO 6346 | 100 | 90 | 90 | 80 | 80 | 70 |
|  | IFO 6348 | 100 | 100 | 90 | 90 | 90 | 90 |
|  | IFO 5364 | 100 | 100 | 100 | 100 | 100 | 100 |

As is clear from the result in Table 1, in all of the preparations, the antibacterial effects after 6 months use were weakened to 70% in IFO 6346 (*Aspergilus terreus*) and 90% in IFO 6348 (*Cladosporium cladosporioides*), while in IFO 5364 (*Geotrichum candidum*) 100% effect was maintained. Namely, all of the preparations in Examples 1 to 7 were found to have the antibacterial effects of at least 70% relative to the original even after 6 month use.

Experimental Example 3
Practical Use Test of the Waterway Narrowing

Preparations 1 to 7 obtained in the above Examples in an amount of each 40 g were placed in a waterway for condensed water (drain) of freezing show-case (manufactured and sold by Sanden Corp, RSO-MS901YB type) and inhibiting effect against narrowing of the waterway by propagation of microorganisms was tested for up to 6 months. The result is shown in Table 2.

In the Table 2, observation of narrowing by propagation of microorganism is shown as X, and no observation thereof is shown as ○.

TABLE 2

|  | After 1 month (%) | After 2 month (%) | After 3 month (%) | After 4 month (%) | After 5 month (%) | After 6 month (%) |
|---|---|---|---|---|---|---|
| Preparation 1 | ○ | ○ | ○ | ○ | ○ | ○ |
| Preparation 2 | ○ | ○ | ○ | ○ | ○ | ○ |
| Preparation 3 | ○ | ○ | ○ | ○ | ○ | ○ |
| Preparation 4 | ○ | ○ | ○ | ○ | ○ | ○ |
| Preparation 5 | ○ | ○ | ○ | ○ | ○ | ○ |
| Preparation 6 | ○ | ○ | ○ | ○ | ○ | ○ |
| Preparation 7 | ○ | ○ | ○ | ○ | ○ | ○ |

As is understood from the result in the Table 2, no narrowing in the drain is observed in all of the preparations, and it is found to be able to inhibit propagation of bacteria, fungi and algae even after 6 months by using the preparations of Examples 1 to 7.

Experimental Example 4
Practical Use Test

To a stainless vat were added 33.5 g of ion-exchanged water, 10.0 g of cetyl pyridinium chloride (manufactured and sold by Wako Pure Chemical Industries, Ltd.; hereinafter cetyl pyridinium chloride is sometimes abbreviated as CPC), 6.5 g of polyvinyl alcohol (manufactured and sold by KURARAY CO., LTD. Trade Name: KURARAY Poval HR-1000) and 0.05 g of disodium ethylenediamine tetraacetate, followed by kneading and melting under heating in an autoclave at 115° C. for 30 minutes. The resulting pale yellow transparent melted solution was dried under reduced pressure of 2 to 3 kPa at 50° C. for 8 hours. The resultant was molded into a plate of about 3 mm thick and further cut to give white pellet preparation(preparation A).

The same process as above except for using 36.0 g of ion-exchanged water and 7.5 g of CPC was conducted to give white pellet preparation(preparation B). The same process as above except for using 38.5 g of ion-exchanged water and 5.0 g of CPC was conducted to give white pellet preparation(preparation C). Each preparations A, B and C obtained as above was placed in a waterway for condensed water (drain) of freezing show-case (manufactured and sold by Sanden Corp., RSO-MS901YB type) and concentration of CPC which is released in the flowing water in the waterway was tested for up to 6 months. The result is shown in Table 3.

| Days | Concentration of CPC (ppm) |  |  |  |  |  |  |  |  |  |
|---|---|---|---|---|---|---|---|---|---|---|
|  | 1 | 10 | 17 | 24 | 31 | 62 | 84 | 123 | 155 | 184 |
| Preparation A | 2.5 | 18.1 | 11.2 | 11.5 | 9.5 | 4.5 | 1.7 | 1.3 | 2.6 | 0.8 |
| Preparation B | 7.3 | 8.1 | 5.7 | 5.4 | 3.9 | 1.5 | 0.8 | 0.4 | 0.9 | 1.1 |
| Preparation C | 4.4 | 5.8 | 6.5 | 3.9 | 4.9 | 0.6 | 0.1 | 0.1 | 0.1 | 0.6 |

As is understood from the result in the Table 3, concentrations of CPC disperse because of variation of flowing water volume, but maintain in 0.1 ppm or more having the anti-bacterial effect even after 6 months, namely the sustained-releasing anti-protista preparation of the present invention is found to keep the anti-bacteria, -fungi and -algae effect even after 6 months use. Especially in use of preparation A and B, concentration of CPC in about 1 ppm even after 6 months use is maintained, and so these two preparations is found to be able to keep the excellent anti-bacteria, -fungi and -algae effect.

Effect of Invention

As mentioned above, the present invention provides a novel sustained-releasing anti-protista preparation (composition), and the said preparation of the present invention can show such an effect as capable of keeping anti-bacteria, -fungi and -algae effect for a long period of time in circulating water in machines and instruments and in waterways for various kinds of waste water.

This patent application is based upon Japanese Patent Application No.2000-123433 and No.2001-99320.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A sustained-releasing composition of an anti-protista substance comprising:
   a water-wettable polyvinylalcohol type polymer having solubility of 1 g or less per 1 liter of water,
   and cetyl pyridinium chloride as an anti-protista substance
   wherein, an amount of cetyl pyridinium chloride in the composition is 10 to 90 wt % of the total composition, and
   a sustained-releasing effect of the anti-protista substance contained in the composition is maintained for 6 months.

2. The composition according to claim 1, wherein a sustained-releasing effect of the anti-protista substance contained in the composition is maintained for 6 months.

3. A sustained-releasing composition of an anti-protista substance,
   wherein a sustained-releasing effect of the anti-protista substance contained in the composition is maintained for 6 months,
   which is obtained by kneading a water-wettable polyvinylalcohol type polymer having solubility of 1 g or less per 1 liter of water with cetyl pyridinium chloride as an anti-protista substance.

4. The composition according to claim 3, wherein after kneading the polyvinylalcohol type polymer and cetyl pyridinium chloride with each other, the resulting mixture is melted under heating and then the obtained melted solution is dried.

5. The composition according to claim 3, wherein the polyvinylalcohol type polymer is polyvinylalcohol.

6. A method for killing of or inhibiting of propagation of a protista in a waterway, comprising allowing flowing water in a waterway to contact with the sustained-releasing composition of claim 1.

7. The method according to claim 6, wherein waterway is a way for waste water in a refrigerator, a freezer, an ice manufacturing machine or a showcase for freezing and cold storage, a way for waste water from an air conditioner, a drainpipe from a sink or a bathroom, a way for waste water from a factory, a trap of a way for waste water or a flush toilet.

8. A waterway comprising the composition according to claim 1.

9. The waterway according to claim 8, wherein said waterway is a wastewater waterway in a refrigerator, a freezer, an ice manufacturing machine, a showcase for freezing and cold storage, or an air conditioner, or is a drainpipe from a sink or a bathroom, a wastewater way from a factory, or a wastewater trap of a toilet.

* * * * *